(12) United States Patent
Wissmath et al.

(10) Patent No.: US 7,834,644 B2
(45) Date of Patent: Nov. 16, 2010

(54) METHOD FOR THE CAPACITIVE DETECTION OF FLAWS IN POLYMER TUBES, AND DEVICE

(75) Inventors: Siegfried Wissmath, Rehau (DE); Florian Rothemund, Rehau (DE)

(73) Assignee: Rehau AG & Co., Rehau (DE)

( * ) Notice: Subject to any disclaimer, the term of this patent is extended or adjusted under 35 U.S.C. 154(b) by 284 days.

(21) Appl. No.: 11/992,425

(22) PCT Filed: Sep. 20, 2006

(86) PCT No.: PCT/EP2006/009138

§ 371 (c)(1),
(2), (4) Date: Mar. 21, 2008

(87) PCT Pub. No.: WO2007/033820

PCT Pub. Date: Mar. 29, 2007

(65) Prior Publication Data

US 2009/0261846 A1    Oct. 22, 2009

(30) Foreign Application Priority Data

Sep. 22, 2005    (DE) .................... 10 2005 045 222

(51) Int. Cl.
*G01R 27/26*    (2006.01)
(52) U.S. Cl. ...................... 324/663; 324/667
(58) Field of Classification Search .............. 324/663, 324/671, 71.1, 71.2

See application file for complete search history.

(56) References Cited

U.S. PATENT DOCUMENTS

| | | | |
|---|---|---|---|
| 2,992,392 A | | 7/1961 | Haynes |
| 4,168,465 A | * | 9/1979 | Prince .................. 324/671 |
| 4,295,092 A | * | 10/1981 | Okamura .............. 324/671 |

FOREIGN PATENT DOCUMENTS

| | | |
|---|---|---|
| DE | 10 95 525 B | 12/1960 |
| DE | 2025 644 | 12/1971 |
| DE | 21 55 509 A1 | 5/1973 |
| DE | 25 05 221 A1 | 8/1976 |
| FR | 2 332 530 | 6/1977 |
| JP | 09 145304 A | 6/1997 |

OTHER PUBLICATIONS

German Search Report dated Jul. 6, 2006, issued in Application No. 10 2005 045 222.1.
International Search Report dated Mar. 22, 2007, issued in Application No. PCT/EP2006/009138.

\* cited by examiner

*Primary Examiner*—Vincent Q Nguyen
(74) *Attorney, Agent, or Firm*—Venable LLP; Robert Kinberg; Ryan M. Flandro

(57) ABSTRACT

A method for detecting flaws in polymer tubes, especially tubes made of crosslinked polyethylene. The tube that is to be tested is exposed to the electric field of a capacitive triple electrode in a housing including a central housing part and housing flanges. The respective flaw generates test signals which are used for marking or eliminating the flaw.

27 Claims, 1 Drawing Sheet

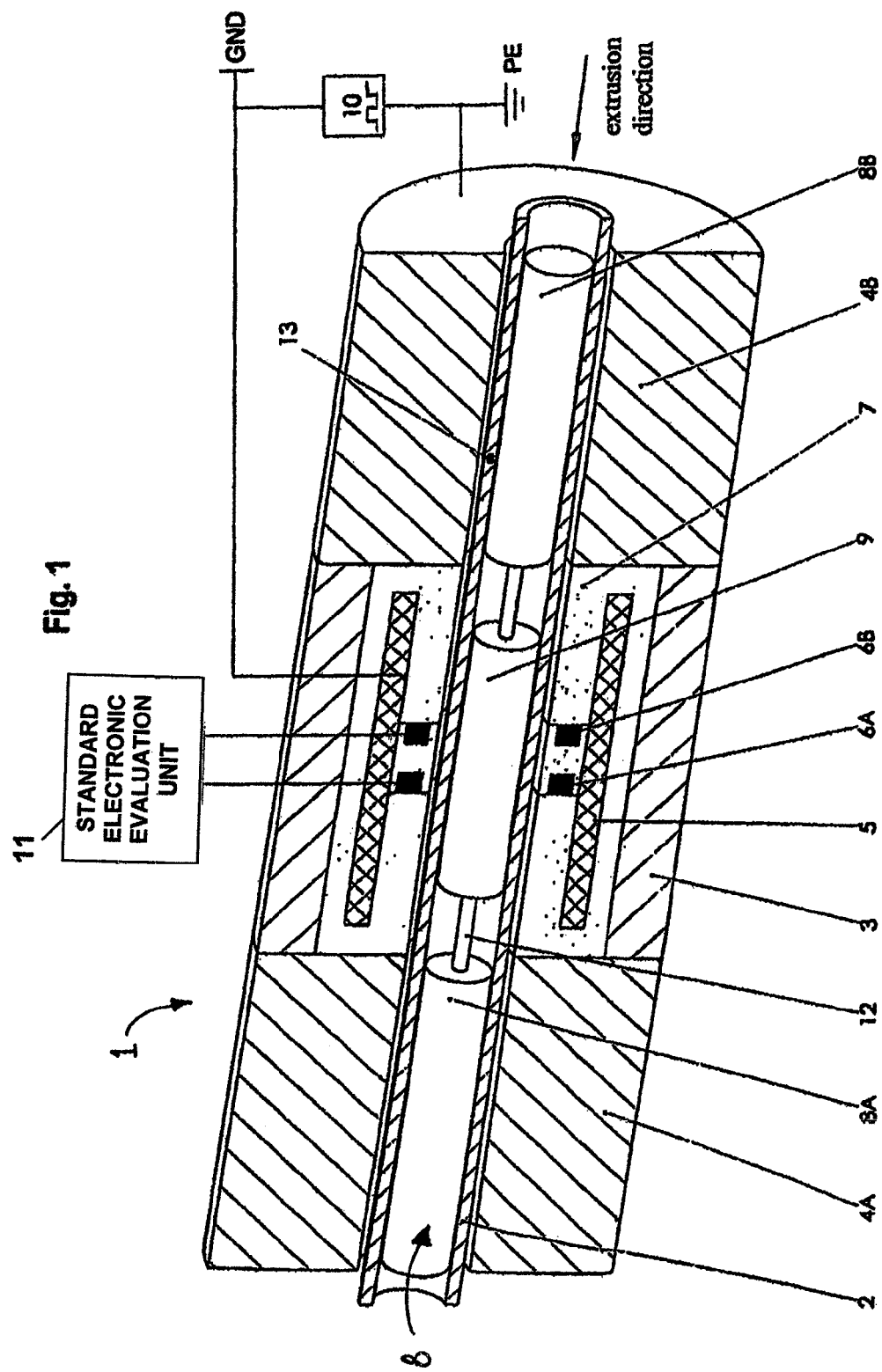

METHOD FOR THE CAPACITIVE DETECTION OF FLAWS IN POLYMER TUBES, AND DEVICE

CROSS-REFERENCE TO RELATED APPLICATION

This application is a U.S. National Phase Application of International Application No. PCT/EP2006/009138, filed Sep. 20, 2006, which claims the priority benefit of German Patent Application No. 10 2005 045 222.1, filed Sep. 22, 2005.

BACKGROUND

1. Field of Invention

The invention relates to a method and a device for the capacitive detection of flaws in polymer tubes, primarily in tubes made of crosslinked polyethylene (PE-X).

2. Related Art

Crosslinked PE-X tubes are mainly used in the building sector, where they are advantageously used as tubes for drinking water, heating, or gas.

Of the three standard methods used for the crosslinking of PE, namely with the aid of energy-rich radiation (PE-Xc), or by adding peroxide (PE-Xa), or through grafting with the aid of trimethoxyvinylsilane (PE-Xb), the yearly tonnage share of the peroxide-crosslinked tubes (PE-Xa) amounts to approximately 31% of the total production of PE-X.

To this day, the crosslinking method using peroxide above all has the disadvantage that the chemical conversion of the peroxide with the PE inside the extruder takes place quantitatively in a very narrow area that is difficult to monitor with process control and thus makes it difficult to monitor the forming of flaws, such as the forming of primary crosslinking products or the bubble-forming. Flaws of this type can lead to premature failure of the tube. For example, serious structural damages can be expected in the case of a sub-floor heating system and, if the tubes are used for gas, can even result in danger to body and life.

Attempts have thus been made from the start to optimize in particular the process technology for producing the tube and, at the same time, to develop reliable methods for detecting flaws in the extruded tube.

The following methods are considered state of the art nowadays for detecting flaws in PE-X tubes:

The High Voltage Method

With the high voltage method, the tube to be tested is pulled through a ring electrode (e.g. a ring-shaped brush electrode), wherein an inner electrode that is connected to ground is positioned at the same location on the inside of the tube. The test voltage is applied between the ring electrode and the inner electrode. The disadvantage of the high-voltage method is that it has a high danger potential because of the applied voltage in the range of approximately 12 to 50 kV and the development of ozone in cases of high-voltage breakdowns, that it depends on the tube wall thickness (outside diameter $\leq 20$ mm) and, above all, the fact that it can detect only specific flaws (hairline cracks, through holes, and foreign matter, including primary crosslinking products). A further restriction is that the flaws must extend over nearly the complete tube wall. The high voltage method in the final analysis is designed to test the electrical insulation properties of a tube.

The Ultrasonic Method

With this method, a distinction must be made between different systems, wherein the system with ultrasonic test heads arranged stationary around a tube respectively can cover only over an extremely small, linear area, while the system with rotating test heads spirally measures and tests the plastic tube. The main disadvantage of the ultrasonic method is the extremely high investment cost, in most cases >100,000 EUR, and the fact that the method is furthermore used primarily for determining the wall thickness and/or the diameter with the aid of a transit-time measurement.

Capacitive two-electrode sensors have recently been used as sensors for detecting labels, in particular transparent labels on transparent substrates.

SUMMARY

It is the object of the present invention to provide a method and the corresponding device for reliably detecting flaws—especially also enclosed flaws—over the complete tube peripheryad the total wall thickness of the tube, wherein this method operates independent of the light permeability of the tube, furthermore does not have the potential for danger with respect to the process and, in particular, is cost-effective.

The essential feature of the method according to the invention is that an electrical field is generated with the aid of a tube-shaped, capacitive electrode, arranged inside a housing, which is adapted to the geometry of the polymer tube to be tested, in connection with at least one receiving antenna and at least one transmitting antenna. The transmitting antenna in this case is positioned in the center section of the housing while the receiving antenna is located in the area of the housing flanges.

The electrical field generated in the center section of the housing is monitored with the aid of ring-shaped measuring electrodes, arranged parallel and in pairs, which encircle the tube to be tested and which detect possible changes in the field with the aid of an electronic display and evaluation unit. The electrical field generated in the region of the housing flanges is transmitted via the receiving antenna and an electrical conductor to the transmitting antenna, which is for the most part locally fixed in the center section of the housing.

The polymer tube to be tested and the air gap between the polymer tube and the capacitive electrodes together form the dielectric.

BRIEF DESCRIPTION OF THE DRAWINGS

The method and the associated device are explained further with reference to FIG. 1.

FIG. 1 shows the device for realizing the method, in a sectional and perspective view.

DETAILED DESCRIPTION

The polymer tube (2) to be tested moves in such a way through the inventive device—preferably immediately following the production process—that the axis of the tube (2) to be tested, which simultaneously also represents the extrusion line, coincides with the longitudinal axis of the device.

If the extruded polymer tube (2) with an enclosed flaw (13) inside the wall moves through the measuring region and past the measuring electrode (6B), which is the closest electrode in movement direction of the polymer tube (2), then the local dielectric changes at that location.

The measuring electrode (6B) consequently receives a disturbed signal while the signal received at the measuring electrode (6A) is still undisturbed.

During the further course of the extrusion, the tube section with the enclosed flaw (13) moves out of the region of the measuring electrode (6B) and into the region of the measuring electrode (6A). As a result, the measuring electrode (6B) once more receives an undisturbed signal while the measuring electrode (6A) now receives a disturbed signal.

According to the invention, at least two measuring electrodes (6A; 6B), arranged as a pair, are necessary because only the comparison of the two signals tapped at the measuring electrodes (6A; 6B) permits a reliable detection of locations containing flaws.

A single measuring electrode, on the other hand, would detect as a flaw a random fluctuation of the capacity of the capacitor.

A further part of the method and/or the device according to an embodiment of the invention is that the housing (1) is connected on the one hand to the positive pole ("hot end") of a high-frequency alternating voltage source (10)—preferably a square-wave signal—and on the other hand to the protective conductor, meaning the earth potential (PE). The capacitive electrode (5) furthermore makes contact with the negative pole ("cold end") of a high-frequency alternating voltage source (10) as well as with the ground (GND). The housing (1), the capacitive electrode (5), and the measuring electrodes (6A; 6B) are insulated electrically against each other.

The respective pairs of signals, received by the measuring electrodes, are fed to a standard electronic evaluation unit (11). The signals are amplified inside input alternating voltage amplifiers, are subsequently rectified via diodes, and are amplified once more with operational amplifiers. The pairs of input signals are then averaged. The output signal, resulting from the averaging of the signals, is compared relative to ground (GND) in an operational amplifier and is then differentiated. This differentiated signal can be used for various actions.

The device according to the invention consists of the following components:

1. The housing (1)

The metal housing (1)—preferably made of aluminum—serves as the supporting element and preferably consists of a tubular body, which can be divided along its longitudinal axis of symmetry for reasons of better access and/or easier assembly.

The metal housing (1) is divided as follows into:

a) The Central Housing Section (3)

The central housing section (3) comprises the electrical connections, the tubular electrode holder (7), and the two housing flanges (4A; 4B). The central housing section is oriented coaxial to the polymer tube (2) to be tested. The tubular electrode holder (7) contains the tubular capacitive electrode (5), the measuring electrodes (6A; 6B) and the electrical insulation of the electrodes relative to each other and relative to the central housing section (3). The metal capacitive electrode (5) is preferably made of aluminum, is tube-shaped, and can be divided along its axis of symmetry for reasons of better access and/or easier assembly. The measuring electrodes (6A; 6B), which are primarily ring-shaped or ring-segment shaped, are electrically conductive electrodes that are preferably made of aluminum and are arranged parallel to each other and in pairs. The spacing between the inside diameter for the measuring electrodes (6A; 6B) and the surface of the polymer tube (2) must be kept to $\leq 5$ mm. According to the invention, the measuring electrodes (6A; 6B) should furthermore be positioned as close to the center as possible inside the capacitive electrode (5). It is advantageous if the measuring electrodes (6A; 6B) are arranged relative to each other in such a way that the following applies with respect to the ratio of the width (b) of a measuring electrode (6A; 6B) to the spacing (w) between the two electrodes:

$$b/w = 0.5 \text{ to } 0.66$$

b) The Housing Flanges (4A; 4B)

The two housing flanges (4A; 4B) are attached on both sides of the cylindrical center housing section (3)—advantageously so as to be detachable—and function to transmit the high-frequency transmitting signal with the aid of capacitive coupling to the transmitting antenna (9), as well as to guide the polymer tube (2) to be tested. The inside diameter of the housing flanges (4A; 4B) and the outside diameter of the polymer tube (2) must be selected so as to achieve an air gap of $\leq 3$ mm, taking into consideration the tube tolerances. The diameter ratio of the polymer tube (2) ($\alpha$) to the measuring electrode (6A; 6B) ($\beta$) to the capacitive electrode (5) ($\gamma$) is preferably 1 to 1.3 to 1.6, wherein the value of $\beta$ can range from 0.6 to 2.0 and the value of $\gamma$ from 0.9 to 2.3.

2. The Inner Electrode

According to the invention, the inner electrode is positioned in the housing (1) region, on the inside of the polymer tube (2) to be tested, and is held locally fixed in a concentric position, preferably by magnetic force. The inner electrode consists of the following components which are connected via an electrical conductor (12):

a) The Receiving Antenna (8)

The receiving antenna (8)—preferably made of aluminum—can consist of a single component or multiple components (8A; 8B). It receives the high-frequency signal from the housing flange (4A; 4B) and conducts this signal to the transmitting antenna (9). The length of the receiving antenna (8) should not exceed the length of the housing flange (4A; 4B) and should amount to 2 to 7 times the diameter of the polymer tube (2). The receiving antenna (8) should furthermore be positioned on the inner electrode, so as to be located as close as possible to the center of the associated housing flange (4A; 4B).

b) The Transmitting Antenna (9)

The transmitting antenna (9) can have a one-part or multi-part design. Together with the capacitive electrode (5) and also the measuring electrodes (6A; 6B), it forms the coaxially arranged, cylinder-shaped capacitive triple electrode. The electro-static fields between the transmitting antenna (9) and the capacitive electrode (5) and/or the transmitting antenna (9) and the measuring electrodes (6A; 6B) homogeneously penetrate the polymer tube (2) to be tested in radial direction. The length of the transmitting antenna (9) of the inner electrode should not exceed the length of the capacitive electrode (5) and, if possible, should be located in the center of the capacitive electrode (5). The ratio of the length ($\delta$) of the transmitting antenna (9) to the length (c) of the capacitive electrode (5) to the length ($\chi$) of the receiving antenna (8) preferably is as follows: $\delta$ to $\epsilon$ to $\chi$=1 to 1.2 to 1.3, wherein the value of $\epsilon$ can range from 1.1 to 2.0 and the value of $\chi$ can range from 1.2 to 2.1.

The invention is explained in the following with the aid of an exemplary embodiment.

The PE-X tube (2) to be tested has an outside diameter of 24 mm and an inside diameter of 20 mm, corresponding to a wall thickness of 2 mm. The tube wall contains a flaw (13) in the form of a filler agglomerate particle with 3 mm diameter, which is fully enclosed.

Following the cooling zone of the extrusion section, the tube enters online the testing device according to the invention, for which the housing parts are respectively embodied as half shells. The air gap between the inside diameter of the cylindrical part of the housing flange (4A; 4B) and the outside diameter of the polymer tube (2) amounts to 1 mm. The spacing between the inside diameter of the measuring electrodes (6A; 6B) and the outside diameter of the PE-X tube (2) is respectively 3 mm. The two measuring electrodes (6A; 6B), respectively consisting of two half rings, are arranged at a distance of 3 mm to each other and have a respective width of 2 mm. The capacitive electrode (5) is composed of two half shells.

The outside diameter of each measuring electrode is 26 mm while the outside diameter of the capacitive electrode is 33 mm.

The capacitive electrode (5) length is 80 mm, the transmitting antenna (9) length is 47 mm, and the total length of the two receiving antennas (8) is 168 mm.

If the extruded polymer tube (2) with the enclosed flaw (13) in the wall moves through the measuring region and past the measuring electrode (6B), which is closest in movement direction of the polymer tube (2), then the local dielectric changes at his location. As a result, the measuring electrode (6B) receives a disturbed signal while the measuring electrode (6B) still receives an undisturbed signal.

During the further course of the extrusion, the tube section with the flaw (13) moves out of the region of the measuring electrode (6B) and into the region of measuring electrode (6A). As a result, the measuring electrode (6B) again receives an undisturbed signal while the measuring electrode (6A) now receives a disturbed signal.

These measuring signals are evaluated and via a switching stage are used for switching a relay, which can be connected to a laser, for example, which marks the beginning and the end of a detected flaw (13) in the polymer tube (2). This flaw is later removed from the tube.

The invention claimed is:

1. A method for detecting a flaw in a crosslinked polyethylene polymer tube passing inside a housing that comprises a housing center section and housing flanges, wherein the method comprises:
   generating an electrical field with the aid of a capacitive triple electrode; and
   subjecting the tube to the electrical field, wherein the respective flaw triggers measuring signals used for marking or removing the flaw.

2. The method according to claim 1, wherein the electrical field is generated inside the housing center section that encloses the tube to be tested, wherein the capacitive triple electrode comprises:
   a tubular capacitive electrode positioned inside the housing center section,
   at least two parallel-arranged, ring-shaped measuring electrodes, and
   a third electrode that functions as transmitting electrode and is held nearly locally fixed inside the tube to be tested.

3. The method according to claim 2, wherein, for generating the electrical field, the capacitive electrode is connected to a negative pole of a high-frequency, alternating voltage source and to the ground.

4. The method according to claim 2, further comprising conducting signals received by the measuring electrodes to an electronic evaluation unit.

5. The method according to claim 4, further comprising utilizing the conducted signals for inline control during the extrusion of the tube.

6. The method according to claim 1, wherein the electrical field is generated between the housing flanges and a receiving antenna located inside the tube to be tested.

7. The method according to claim 1, wherein, for generating the electrical field, the housing flanges are connected on the one hand to a positive pole of a high-frequency, alternating voltage source and to a protective conductor comprising the earth potential.

8. The method according to claim 7, wherein the high-frequency, alternating voltage source provides a square-wave signal.

9. A device for detecting a flaw in a crosslinked polyethylene polymer tubes, said device comprising:
   a housing including a housing center section and a housing flange through which the tube to be tested passes;
   a capacitive triple electrode configured to generate an electrical field and comprising:
      a tubular capacitive electrode and a measuring electrode disposed within an electrode holder; and
      a receiving antenna and a transmitting antenna coupled by an electrical conductor and disposed within the tube to be tested;
   a high-frequency, alternating voltage source coupled to the tubular capacitive electrode; and
   an electronic evaluation unit connected to the measuring electrode and configured to receive signals therefrom triggered by the flaw.

10. The device according to claim 9, wherein the housing is tube-shaped and metal.

11. The device according to claim 9, characterized wherein the housing center section comprises the electrode holder, and wherein the capacitive electrode and measuring electrode are electrically insulated relative to each other and from the housing and electrical connections.

12. The device according to claim 9, wherein the transmitting antenna is arranged in the area of the housing center section, inside the polymer tube to be tested.

13. The device according to claim 9, wherein the housing flange comprises two housing flanges, detachably secured to both sides of the housing center section, are configured to transmit a high-frequency transmitting signal to the receiving antenna and to guide the polymer tube to be tested.

14. The device according to claim 9, wherein the housing with the electrode holder disposed therein is divided multiple times along its longitudinal axis of symmetry for reasons of better access and/or easier assembly.

15. The device according to claim 9, wherein an inside diameter of the housing flange and an outside diameter of the polymer tube define an air gap therebetween of $\leq 3$ mm.

16. The device according to claim 9, wherein the measuring electrodes comprises aluminum rings or segmented rings arranged in a pair, parallel to each other.

17. The device according to claim 9, wherein a spacing between an inside diameter of the measuring electrode and the surface of the polymer tube is $\leq 5$ mm.

18. The device according to claim 9, wherein the measuring electrode comprises two measuring electrodes positioned centrally inside the capacitive electrode, and wherein the measuring electrodes are arranged in such a way that a ratio of a width (b) of one of the measuring electrodes to a distance (w) between the measuring electrodes is:

$$b/w = 0.5 \text{ to } 0.66.$$

19. The device according to claim 9, wherein a ratio of a diameter (α) of the polymer tube to a diameter (β) of the measuring electrode to a diameter (γ) of the capacitive electrode is α to β to γ=1 to 1.3 to 1.6, wherein β=0.6 to 2.0, and γ=0.9 to 2.3.

20. The device according to claim 9, wherein the receiving antenna, which comprises aluminum and receives a high-frequency signal from the housing flange, is connected to the transmitting antenna via the electrical conductor and, wherein the receiving antenna is locally fixed by magnetic force and concentric with the housing flange.

21. The device according to claim 9, wherein a length of the receiving antenna is 2 to 7 times a diameter of the polymer tube and does not exceed a length of the housing flange.

22. The device according to claim 9, wherein the receiving antenna is positioned on the electrical conductor in a center of the housing flange.

23. The device according to claim 9, wherein the transmitting antenna in connection with the capacitive electrode, the measuring electrode and the housing center section generates electrostatic fields, which homogeneously penetrate the polymer tube to be tested in a radial direction.

24. The device according to claim 9, wherein the transmitting antenna is arranged centrally in the area of the capacitive electrode, and wherein a length of the transmitting antenna does not exceed a length of the capacitive electrode.

25. The device according to claim 9, wherein a ratio of a respective length (δ) of the transmitting antenna to a length (ε) of the capacitive electrode to a length (χ) of the receiving antenna is:

δ to ε to χ=1 to 1.2 to 1.3 wherein the value of ε is between 1.1 and 2.0 and the value of χ is between 1.2 and 2.1.

26. The device according to claim 9, wherein the transmitting antenna and/or the receiving antenna comprises one-part design or a multi-part design.

27. The device according to claim 9, wherein the measuring electrode comprises at least two measuring electrodes arranged in a pair.

* * * * *